United States Patent [19]

Fleming

[11] Patent Number: 5,608,520
[45] Date of Patent: Mar. 4, 1997

[54] PLASMA EMISSION SPECTROSCOPY METHOD OF TUMOR THERAPY

[75] Inventor: Kevin J. Fleming, Albuquerque, N.M.

[73] Assignee: The United States of America as represented by he Department of Energy, Washington, D.C.

[21] Appl. No.: 455,269

[22] Filed: May 31, 1995

Related U.S. Application Data

[62] Division of Ser. No. 272,461, Jul. 11, 1994, abandoned.

[51] Int. Cl.$^6$ ............... G01J 3/30; A61B 5/00; A61B 6/00
[52] U.S. Cl. .......... 356/318; 128/633; 128/665
[58] Field of Search ............... 356/445–446, 356/317–318; 250/227.2, 239; 348/61, 65, 67, 73, 77–78, 94–95; 128/633, 665, 664

[56] References Cited

U.S. PATENT DOCUMENTS

| | | | |
|---|---|---|---|
| 4,076,421 | 2/1978 | Kishner | 356/210 |
| 4,756,619 | 7/1988 | Gerlinger et al. | 356/319 |
| 4,768,513 | 9/1988 | Suzuki | 356/318 |
| 4,781,676 | 11/1988 | Schweighardt et al. | 604/21 |
| 4,919,535 | 4/1990 | Hohberg et al. | 356/429 |
| 4,932,412 | 6/1990 | Goldenberg | 128/654 |
| 4,957,476 | 9/1990 | Lano | 600/7 |
| 4,973,848 | 11/1990 | Kolobanov et al. | 250/458.1 |
| 4,981,138 | 1/1991 | Deckelbaum et al. | 128/665 |
| 4,995,723 | 2/1991 | Carlhoft et al. | 356/318 |
| 5,042,494 | 8/1991 | Alfano | 128/665 |
| 5,301,681 | 4/1994 | DeBar et al. | 128/736 |
| 5,305,759 | 4/1994 | Kaneko et al. | 356/318 |
| 5,365,267 | 11/1994 | Edwards | 348/65 |
| 5,408,996 | 4/1995 | Salb | 128/665 |
| 5,421,339 | 6/1995 | Ramanujam et al. | 128/665 |
| 5,470,568 | 11/1995 | Lee | 604/20 |

OTHER PUBLICATIONS

Fleming et al "Portable, Solid State, Fiber Optic Coupled Doppler Interferometer System for Detonation and Shock Diagnostics".

*Primary Examiner*—Frank Gonzalez
*Assistant Examiner*—Jason D. Eisenberg
*Attorney, Agent, or Firm*—Russell D. Elliott; James H. Chafin; William R. Moser

[57] ABSTRACT

Disclosed are a method and apparatus for performing photon diagnostics using a portable and durable apparatus which incorporates the use of a remote sensing probe in fiberoptic communication with an interferometer or spectrometer. Also disclosed are applications for the apparatus including optically measuring high velocities and analyzing plasma/emission spectral characteristics.

3 Claims, 6 Drawing Sheets

5,608,520

PLASMA EMISSION SPECTROSCOPY METHOD OF TUMOR THERAPY

GOVERNMENT RIGHTS

The U.S. Government has rights in this invention pursuant to Contract No. DE-AC04-76DP00789 between the U.S. Department of Energy (DOE) and AT&T Technologies Inc.

This application is a divisional of application Ser. No. 08/272,461, filed Jul. 11, 1994, now abandoned, the entire contents of which are hereby incorporated by reference.

BACKGROUND OF THE INVENTION

1. Field of the Invention

This invention relates generally to the field of photon diagnostics including displacement or Doppler interferometry, and more particularly, to a portable and durable apparatus which incorporates the use of a remote sensing probe in fiberoptic communication with an interferometer or spectrometer. Also disclosed here are several applications for the apparatus including optically measuring high velocities and analyzing plasma/emission spectral characteristics. Applications for the apparatus include analyzing shock wave effects and detecting and destroying tumors in living tissue.

2. Description of the Related Art

Interferometric analysis concerns a group of techniques whereby a beam of light from a luminous area is separated into two or more parts by creating partial reflections, the parts being subsequently reunited after traversing different optical paths. Interferometers are capable of precise measurement of very small distances by analysis of interference "fringes". Phase differences between the isolated portions of the original beam of light generate interference "fringes" which bear a unique relationship to the wavelength of light used. Displacement and Doppler shift interferometry are methods used for detecting motion on a surface without mechanical contact which could change the natural motion of the surface.

Spectral analysis includes plasma and emission spectroscopy. Plasma spectroscopy involves using a focused high powered laser to ablate material, thereby convening it into an ionized plasma which has a spectral linewidth unique to the molecular/atomic make-up of the material which is ablated. Emission spectroscopy uses a low to medium powered laser to stimulate a target material to radiate a wavelength of light different from that of the laser.

VISAR (Velocity Interferometer System for Any Reflector) is a specialized Doppler interferometer system that optically measures acceleration, displacement and velocity using coherent, single frequency laser light to illuminate a target that exhibits reflectivity. Reflected light is analyzed using a modified unequal leg Michelson interferometer. VISAR was first developed by Barker and Hollenbach as a means for measuring particle velocities of materials in gas gun experiments. (L. M. Barker and R. E. Hollenbach, "Laser Interferometer for Measuring High Velocities of Any Reflecting Surface," *Journal of Applied Physics* 43:11, November, 1972). It has been modified and refined over the years since its initial introduction, and it has become the world-wide accepted standard for shock phenomena analysis.

Certain limitations are inherent in traditional laser spectroscopy, VISAR and other Doppler interferometry methods as a result of the equipment having large power and cooling requirements and a sensitive and complex nature. Also, existing VISAR technology requires the use of an open and potentially hazardous laser beam. Consequently, many interferometric applications have been typically restricted to use in controlled laboratory situations. Nevertheless, many times there is a need to locate either the light source or the interferometer, itself, at a distance remote from the target to be analyzed. For example, in instances where explosions or detonations could alter data or cause damage to instruments, it would be desirable to remotely gather data for analysis in real time. Likewise, situations in which a target is either inaccessible or in a location which is hazardous to human beings would necessitate remote data acquisition. Also, there are cases where it may be desirable to perform interferometric analysis while minimizing disturbance to surrounding structures, such as within human or animal tissues.

Existing methods for directing a laser beam to a target require locating the laser and diagnostic apparatus close to the target (within approximately 30 meters) and using mirrors to direct the laser beam to and from the surface being analyzed. This precludes effective use of VISAR, other forms of open-beam interferometry and laser spectroscopy in analysis under conditions wherein the "line of sight" of the laser beam is interrupted, such as through smoke or dust or inside tunnels or enclosed chambers. Also, since the instrumentation involved in the production of the laser beam and collection and analysis of reflected or emitted light is bulky and sensitive, and subject to corruption and degradation by environmental factors, photon analysis as it is practiced using presently available technology is often not well suited to field use or applications in harsh environments.

There is an ongoing need in the field of photon analysis for versatile instruments which are rugged and durable and which exhibit remote sensing capability.

BRIEF SUMMARY OF THE INVENTION

In view of the needs described above, it is an object of the present invention to provide a device for use in remote interferometric applications.

It is another object of the present invention to provide a device for use in remote spectroscopic applications.

It is another object of the present invention to provide an efficient light sending and receiving device.

It is another object of the present invention to provide a device that is rugged and durable and able to withstand the rigors of field use.

It is yet another object of the present invention to detect and relay a signal indicating the optimum distance-to-target for the front focusing lens.

It is another object of the present invention to provide a device that can use different laser wavelengths without alteration of the device.

It is another object of the present invention to provide a device that is lightweight and compact with various provisions for mounting on optical tables, camera tripods, other support means and in the context of robotic applications.

It is another object of the present invention to provide a device capable of analyzing material structure of a surface by ablating layers of the surface and identifying the atomic or molecular make-up of the ablated material.

It is another object of the present invention to provide a device that includes fittings or sockets to allow users to plug in and unplug fiberoptic cables associated with the device without compromising or changing the optics of the device.

It is another object of the present invention to provide a device including fittings and associated fiberoptic components assembled so as to maximize the light gathering efficiency of the device.

It is another object of the present invention to provide a device capable of effectively utilizing high-power to perform photon analysis.

It is another object of the present invention to provide a device which includes fiberoptics exhibiting a power density capability of up to 5 gigaWatts/cm$^2$.

It is yet another object of the present invention to provide a device that includes a means to permanently affix collecting optics and fiberoptic receptacles to a remote sensing device thereby eliminating risk of misalignment and the need for adjustments to compensate for changes in the positions of such collecting optics and fiberoptic receptacles.

It is another object of the present invention to provide a device that includes a flexible system which can use a variety of different lenses and operating distances for different applications.

It is another object of the present invention to provide a device that includes a system of lenses which allows a front focusing lens to be removed from its housing and positioned so as to function up to several meters in front of the housing.

It is another object of the present invention to provide a device that incorporates, at the user's option, a video camera which is integrated into the probe to facilitate remote viewing of a target using the same optics through which the laser is focused.

It is another object of the present invention to provide a device that incorporates a variable wavelength-selective attenuator controlling laser light entering the video camera, if used.

It is yet another object of the present invention to provide a device that combines remote sensing probe applications with real-time photon analysis of biological tissues.

It is yet another object of the present invention to provide a device capable of plasma spectroscopic or emission spectroscopic analysis of ionized light generated by vaporized tissue.

Upon further study of the specification and appended claims, further objects and advantages will become apparent to those skilled in the art. The objects have been fulfilled by the device of the present invention which comprises a laser interferometer or spectrum analyzer, coupled fiberoptically to a remote probe containing sophisticated optics. In a preferred embodiment, the probe and fiberoptic connectors are constructed ruggedly such that they can endure physical stresses associated with field use without compromise to the optical capabilities of the devil.

DETAILED DESCRIPTION

Figure 1:
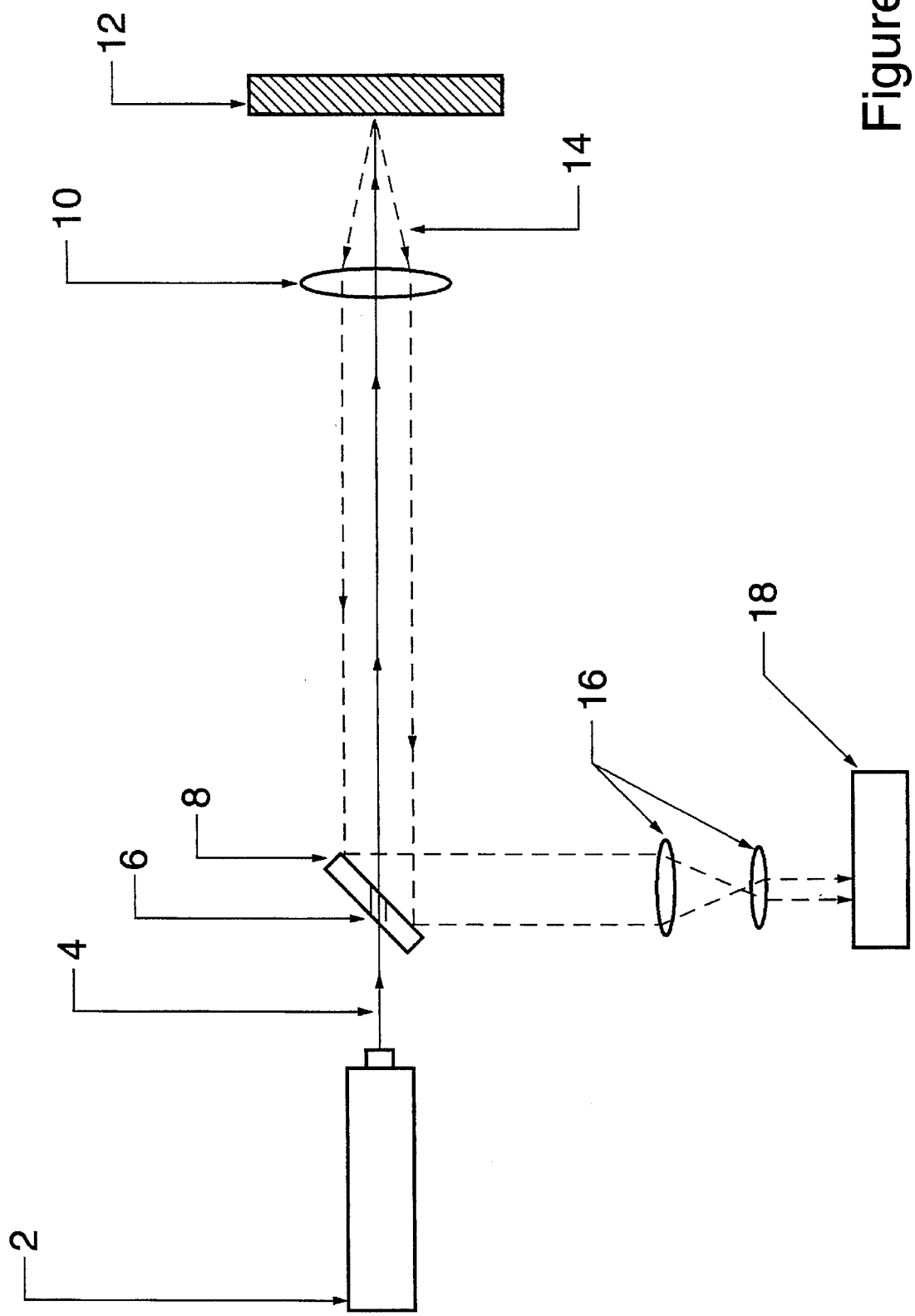
FIG. 1 illustrates existing art and is a schematic depiction of optics in a typical experimental set up without the present invention.

In order to fully appreciate the potential value of the present invention, it is helpful to briefly describe optics used in Doppler shift interferometry without the improvements provided by the device claimed herein. FIG. 1 illustrates the optics of a typical experimental set up without the invention. A laser 2 directs a laser beam 4 through a hole 6 in a turning mirror 8. The beam is then focused on a target 12 by a focusing lens 10. Diffuse light 14 then reflects from the target and travels back toward the same focusing lens 10 which collimates the reflected light. This collimated reflected light is then directed by the mining mirror 8 to a reducing and collimating lens pair 16. The light thus reduced and collimated enters an interferometer 18 where it is finally analyzed as an electronic signal.

According to a typical experimental configuration such as this, proper alignment of all of the components is critical to successful data acquisition. In addition, FIG. 1 illustrates that the paths of the original laser beam and the reflected light must be uninterrupted.

Figure 2:
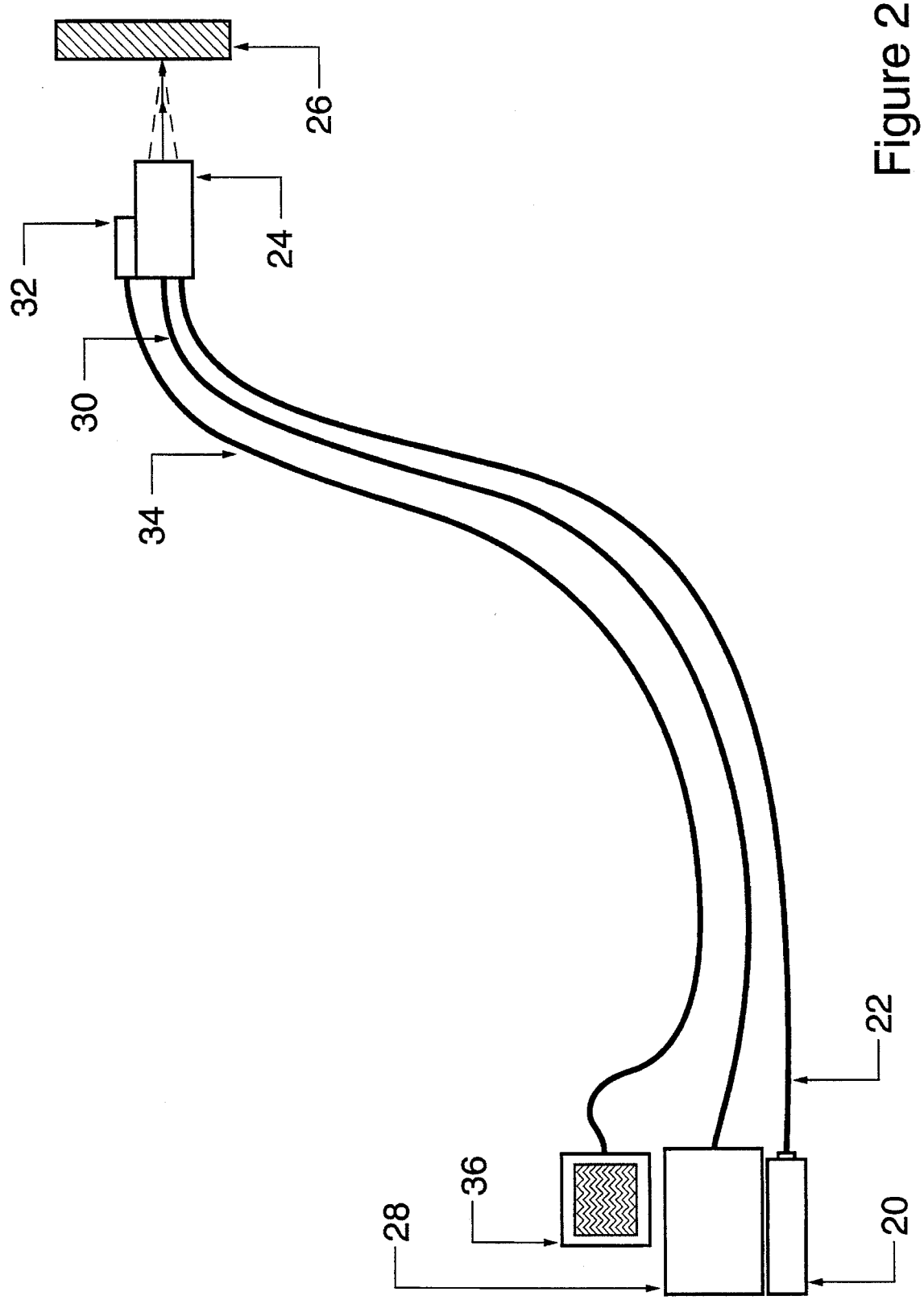
FIG. 2 schematically illustrates use of the remote probe of the present invention.

In one aspect, the present invention provides an apparatus with which interferometric data may obtained remotely from the interferometer, itself. In addition, the critical optics are contained within a durable probe which can be manipulated easily without compromising the sensitivity of the instrument. In FIG. 2, a laser 20 sends a laser beam into a first fiberoptic 22 which carries the beam to a remote probe 24 containing optical structures which are described in detail below. The laser beam is then focused by the probe on a target 26 where diffuse light is reflected back into the probe. The optics contained within the probe then send the reflected light into a second fiberoptic 30 which carries this light to an interferometer 28 where interferometric analysis is performed. Another feature illustrated in FIG. 2 is the use of a camera 32 in communication with a monitor 36 via a coaxial cable 34. This option allows for real-time viewing of the target during the period of data acquisition.

Figure 3A:
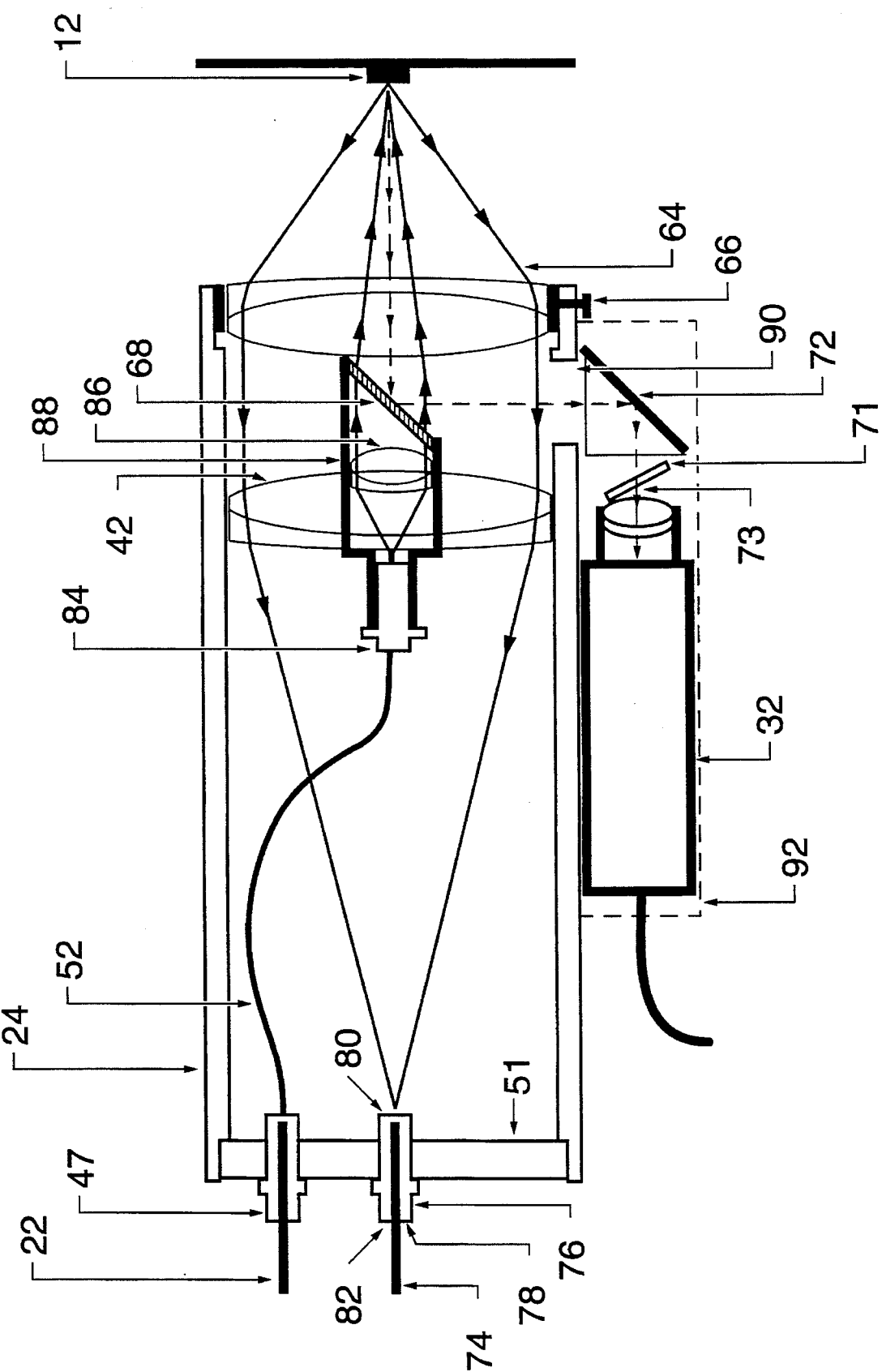
FIGS. 3(a), and 3(b) drawings of preferred embodiments on the device of the present invention.

FIG. 3(a) is a detailed drawing showing a preferred probe configuration. A sending fiberoptic 22 from a laser is connected to the probe 24 via an input fiberoptic coupler 47 comprising an external input connector positioned outside of the housing, an internal input connector positioned inside the housing and an input flowthrough positioned therebetween. This fiberoptic coupler configuration allows for dismantling in case repair in needed. The input fiberoptic coupler adjoins an internal fiberoptic 52 placed within the probe. The internal fiberoptic 52 is supported by a fiber supporting connector 84 which is mounted along the central axis of the probe. The internal fiberoptic 52 is inserted through an aperture in the fiber supporting connector 84 with the terminus of the fiber located at the focal length of a collimating lens 86 which is mounted in an internal lens and mirror support 88. A beam of laser light exits the terminus of the fiber 52 and is collimated by the collimating lens 86 and is allowed to pass through a dichroic mirror 68 where it is focused by a target focusing lens 64 at the front of the probe onto a target 12. In the case of interferometric analysis of a target, light is reflected from the target and collected and collimated by the same lens 64. The light is then allowed to pass through a terminal focusing lens 42 where it is focused to the center of an output fiberoptic coupler 76 which is mounted in the rear of the probe housing 51. An external collecting fiberoptic 74 then carries the light signal to an interferometer. In the case of spectroscopic analysis, the light entering the probe is emitted by the target itself, or is generated as a flash due to laser ablation.

Where the remote viewing option is employed, a portion of the light entering the probe from the target is directed by the target focusing lens 64 towards the dichroic mirror 68 whereupon the spectra of light not allowed to pass through the dichroic mirror is turned and directed through a port 90 in the probe housing. This light is then deflected by a turning mirror 72 and directed through a video camera 32. The camera may be mounted externally and parallel to the probe housing, perhaps encased in a separate camera housing 92. It may be desirable to interpose in the path of light traveling from the turning mirror to the camera a variable (wavelength selective) laser light attenuator (which is a long-pass or short-pass filter) suitable for reducing laser light intensity while allowing ancillary lighting to remain constant as it enters the camera. Otherwise, the camera can be saturated. In the figure, this attenuator 71 is depicted as being rotatable about an axis 73 whereby the angle at which the attenuator is positioned determines the precise wavelengths allowed to pass and enter the camera so as not to overload the camera and diminish the clarity of the image recorded by the camera. Light attenuators of this type are well-known in the art and those skilled in the art will be familiar with their use.

The dichroic mirror 68 has a coating such that it will allow a particular wavelength or wavelengths of light to pass through while other wavelengths of light are reflected..This allows simultaneous viewing of the target with a video camera 32 without impeding the light going to the collecting fiber 74. If different wavelengths of lasers are to be used, the dichroic mirror can be specified as long-pass or short-pass. For example, if the laser wavelengths being used are less than 700 nm, a short-pass dichroic mirror could be used that will transmit 750-nm wavelengths and less. The target can then be illuminated with normal lighting which has wavelengths above 750 nm which will also be collected and routed to the video camera. Normal video cameras are sensitive from a visible (400 nm) to infrared (1200 nm) wavelength. Dichroic mirrors are not perfect and will reflect a small portion of the laser light being used. This is an added benefit since the camera will not only see the target but will also display the laser spot on the target. The turning mirror 72, if used, will reflect a very wide spectrum of light and requires no special coating.

Mounted at the rear of the probe housing is an output fiberoptic coupler 76 comprising an external output connector 78 positioned outside of the housing, and internal output connector 80 positioned inside the housing, and an output feedthrough 82 positioned therebetween. Attached to the external output connector is a second external fiberoptic 74 leading to an interferometer. The output fiberoptic coupler is positioned such that light focused by the terminal focusing lens is collected by a second external fiberoptic.

Positioned at the front of the probe is a target focusing lens which can be secured by a set screw 66. This permits the target focusing lens to be removed and set in front of the probe itself according to a method of use described more in detail below.

The sending/collimating lens 86 can be of a variety of focal lengths and diameters but certain factors need to be addressed for proper operation. A larger beam diameter will stay collimated longer than a beam of smaller diameter, allowing for longer distances between the target and device. Also, a smaller sending fiber with a small numerical aperture will be collimated for a longer distance as compared with one with a larger numerical aperture. (Numerical aperture for fibers is the sine of the half angle of the maximum angle that light will be coupled into a fiber. A significant benefit associated with the device of the present invention concerns the fact that experimentally it has been shown that very high power can be used to operate the fiberoptic probe.) Working devices have been successfully used to collect data as far as 0.5 kilometers from the target.

As mentioned above, the target focusing lens 64 can be removed and placed several meters away from the remainder of the probe as long as laser light passes through the center of the lens and the lens is not cocked to the incident beam. Since the incident beam from sending/collimating lens 86 is collimated (i.e. infinite conjugate ratio), any focal length target focusing lens 64 can be used without any changes to the invention.

In a typical run, the target focusing lens 64 is set at its focal length from the target. When this is so, the reflected light will be of maximum intensity and, upon passing back through the target focusing lens this reflected light will be collimated.

The collecting/focusing lens 62 and terminal focusing lens 42 work together to focus the return light to a spot in the center of output fiberoptic coupler 76. The reason for using two lenses is to reduce the focal distance of the light, thereby compacting the overall length of the device. Also, the shorter focal length reduces the diameter of the focused spot and allows more of the light to enter the collecting fiber. The lenses are selected and spaced apart such that their effective numerical aperture is less than the numerical aperture of the collecting fiber 74 being used. Persons skilled in the art can define the proper lenses and separation distance. Commercial achromat lenses which are insensitive to wavelength variation and focus well are used in the preferred embodiment.

Figure 3B:
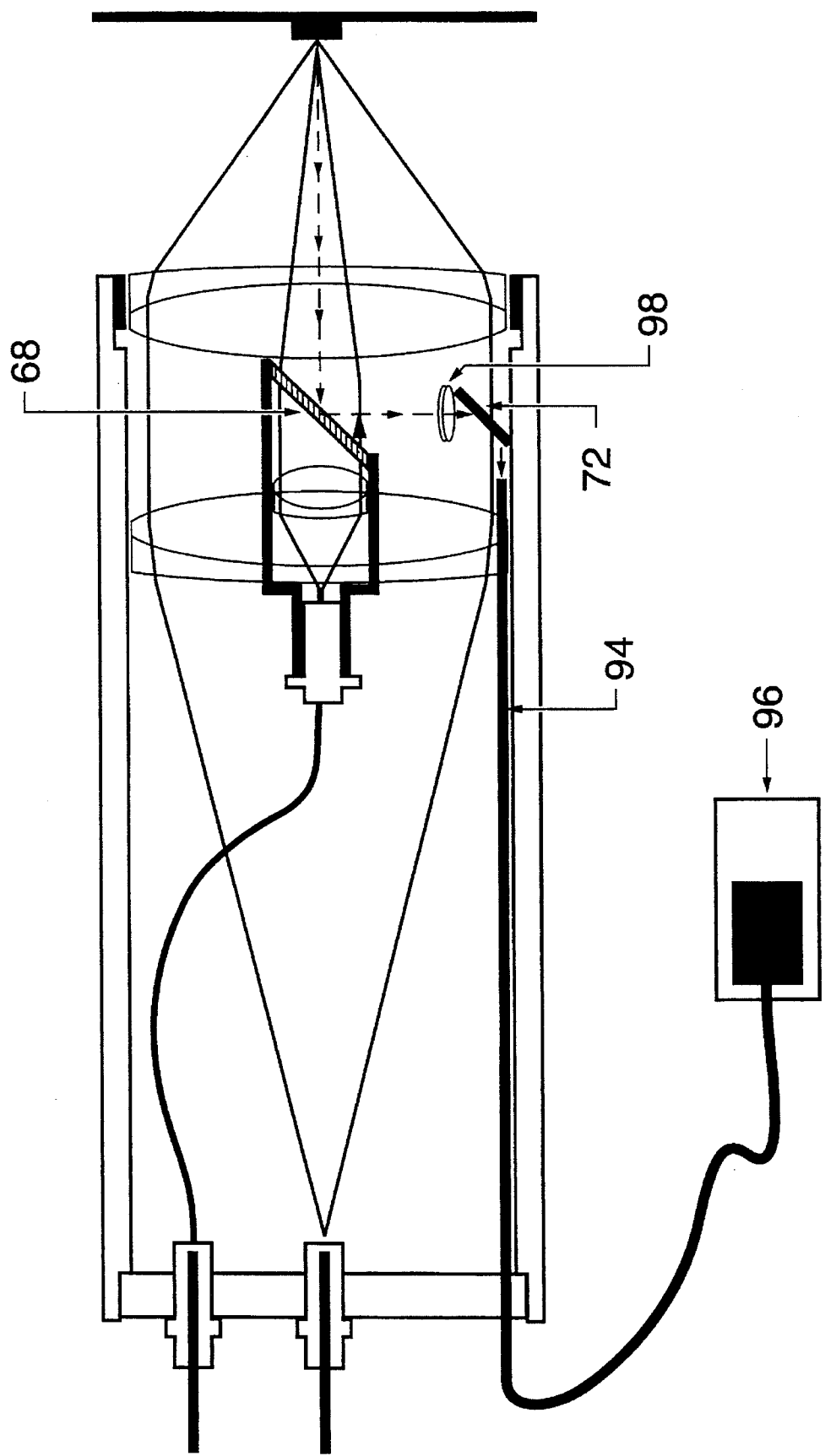
Figure 4:
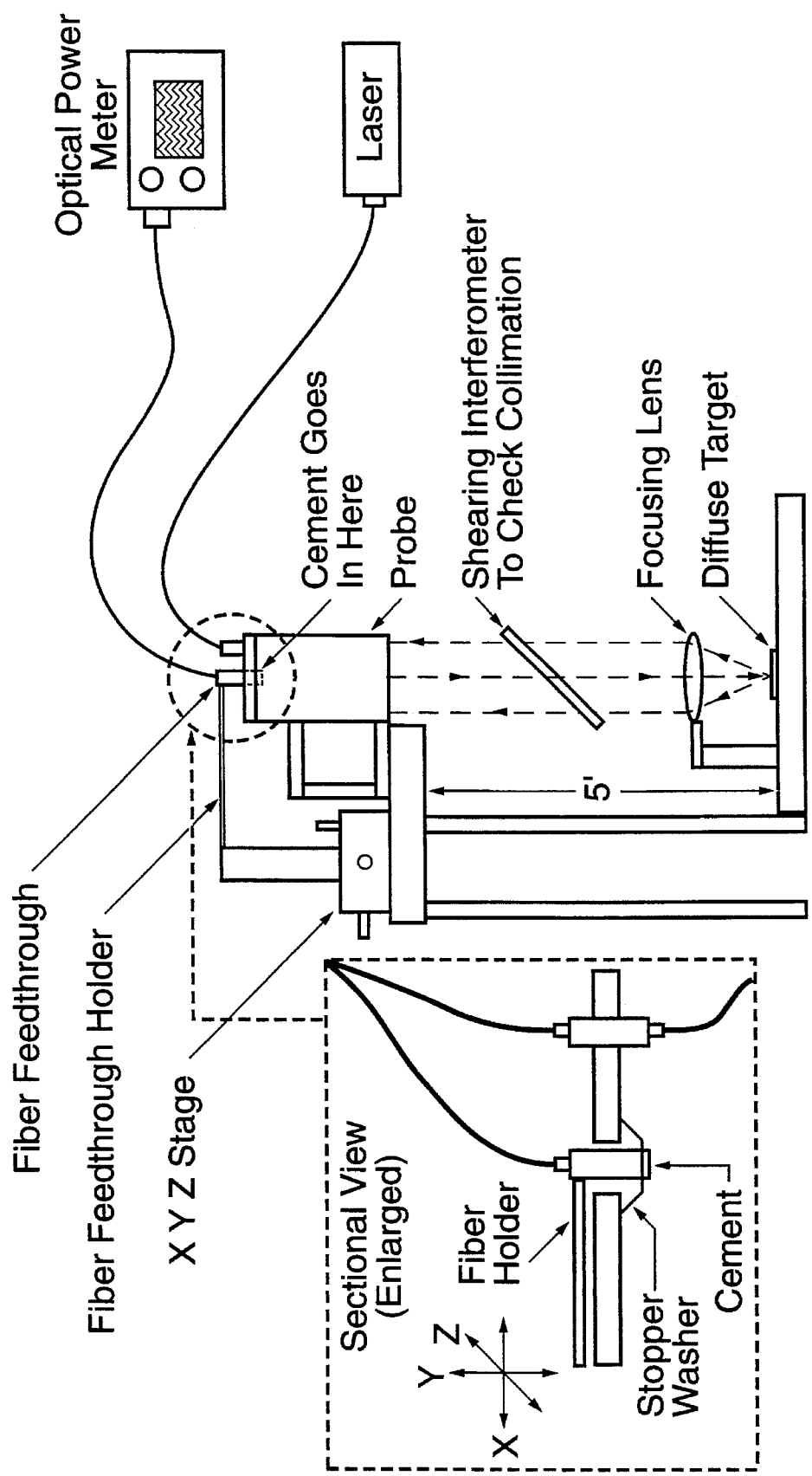
FIG. 4 shows a preferred method for ensuring the optics of the apparatus are properly aligned.

FIG. 3(*b*) is a detailed drawing showing a variation on the configuration depicted in FIG. 3(*a*). Optically, the probe functions identically to that shown in FIG. 3(*a*) with the exception that fiberoptic imaging conduit and a remote video camera/video monitor arrangement are used in place of a camera attached to the probe, itself. As shown in FIG. 4(*c*), a focusing lens 98 is interposed in the path of light from the dichroic mirror 68 to the turning mirror 72. Focused light reflected off of the turning mirror then enters one end of a fiberoptic imaging conduit 94 positioned inside of the probe, itself. The conduit is positioned such that it passes through the probe housing and to the outside, with the other end of the conduit in communication with a video camera and monitor assembly 96. Clarity of the video image will determine the necessary position of the focusing lens 98. Techniques for affixing conduit to and through the housing, and the use of video monitoring equipment in communication with fiberoptic imaging conduit, are well known in the art. The reason for this derivation from the primary sensor design depicted in FIG. 3(*a*) is to reduce the physical size of the body and to remove the electrically driven camera which could fail in high radiation or electromagnetic environments.

In any of the above configurations, the collecting fiberoptic and associated feedthrough must be placed precisely if maximum coupling efficiency is to be achieved. Normal machining practices are inadequate for this purpose and a special fabrication method is required. FIG. 4 illustrates the preferred method for alignment of the rear housing and return signal fiber feedthrough. Reference is made to FIGS. 3(*a*), 3(*b*) and 5 in the overview of the setup that follows. First, the focal point of the lens pair 42, 64 is calculated. The equation $f1*f2/(f1+f2)-d$ is used where $f1, f2$ are the respective focal lengths of the lenses and d equals the separation distance of the lenses. After determining the position of the lens pair in the main housing and the focal point of the lens pair, the main housing is fabricated such that the back end of the housing is approximately 0.100 inches longer than the final focal point of the lens pair. A hole is bored in the center of the rear housing such that the, diameter of the feedthrough 82 is 0.100 inches smaller than the hole in the housing. A stopper washer 100 is made out of aluminum foil or a similar material and is inserted on the feedthrough 82. The feedthrough is then slipped on the rear housing which is then attached to the main housing 49 with screws or adhesive with locating dowels. With the fiber 74 connected to the feedthrough, the feedthrough is then clamped to an x-y-z stage. The input fiber 22 is then connected to the laser and the laser is energized. A target is set up facing upward and the device is mounted approximately five feet above the target, The focusing lens 64 is removed and set at its focal distance above the target. With the laser operating, the focusing lens is adjusted until there is a collimated return beam. (A shearing interferometer will measure collimation.)

The end of the receiving fiber 74 is then connected to an optical power meter. The x-y-z stage in all axes is slowly translated until a maximum reading on the meter is obtained. A slow shrinkage epoxy or similar viscous adhesive 102 is mixed and used to fill the void between the fiber feedthrough 82 and the rear housing bored hole. The stopper washer 100 will contain the cement 102 to the hole. For optimal results, one should wait at least the cure time of the cement before removing the finished device.

Since there will always be a collimated return beam from the focusing lens no matter what the focal length is, the maximum power that is coupled into the receiving fiber will inform the operator that the lens is optimally placed. This will eliminate the normal steps associated with correctly placing the lens at its focal length from the target.

Figure 5:
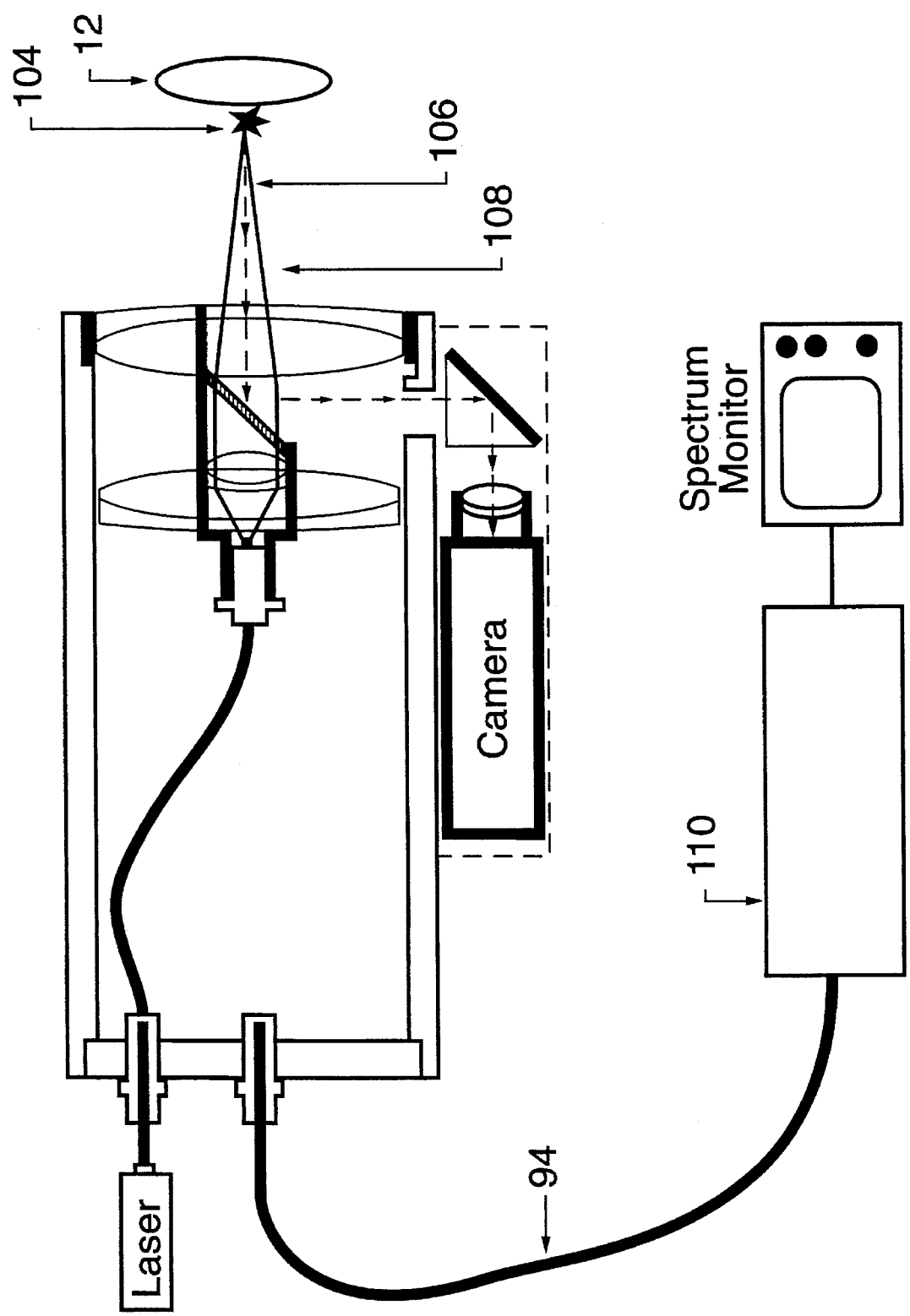
FIG. 5 illustrates a method by which the apparatus of the invention may be used to remove tumors.

FIG. 5 is an illustration of a method by which the invention may be used in removing tumors. Referring to FIG. 5, the target 12 which in this case might be a tumor, is viewed using a camera or imaging conduit as describe earlier. The patient may be injected with HPP or a similar chemical which is selectively absorbed by cancerous tissue and fluoresces when excited by laser radiation. A flash 104 from the surface ionized by the laser and an electronic signal would be generated in the same fashion as earlier described wherein incoming light 106 would be, in part, deflected to the camera or imaging conduit to permit viewing of the target, and collected light 108 from the ionized surface would be directed via fiber optic 74 to a spectrum analyzer 110. Data from the spectrum analyzer would then be displaying on a spectrum monitor. Using this method, a tumor could either be detected or ionized, using multiple wavelength laser light from the probe as the source inducing fluorescence. The substance selectively absorbed by the cancerous tissue will exhibit a unique spectral emission upon ionization and formation of plasma. In the case where that spectral emission is distinct from emissions associated with ionization of normal, healthy tissue, the boundary between cancerous and noncancerous tissue can be distinguished. Comparing spectral data in a succession of ionizations, the extent and location of cancerous tissue can be identified.

Using a similar configuration, a probe may be used for laser welding, classical spectrum analysis, silicon wafer processing, or environmental contamination analysis wherein a laser is used to remove layers from material, and the spectrum analyzer detects differences in target material as portions of the target material are removed.

Without further elaboration, it is believed that one skilled in the art can, using the preceding description, utilize the present invention to its fullest extent. The preceding description is generic in that the invention will work for Doppler interferometry or plasma/emission spectroscopy. Having thus described the invention, it would be obvious to those of ordinary skill in the art that various modifications can be made within the spirit and scope of the present invention. It is intended to encompass all such variations as fall within the scope and spirit of the invention.

I claim:

1. A method of tumor therapy comprising the steps of:

providing a fiberoptic photon analysis sensor in operative association with a spectral analysis means, said remote fiberoptic photon analysis sensor comprising a lens having a focal length, placing said fiberoptic photon analysis sensor in proximity to tissue in a patient so that said tissue in said patient is within said focal length of said lens, injecting said patient with a substance that is selectively absorbed by cancerous tissue, which substance exhibits a unique spectral emission upon ionization, and which unique spectral emission is different from that of healthy tissue when ionized, using a laser to cause ionization of said tissue in said patient, and distinguishing cancerous from noncancerous tissue in said patient by analyzing, using said spectral analysis means, plasma generated as a result of said ionization for presence of said spectral emission which is different from that of healthy tissue when ionized.

2. The method of claim 1 further comprising the steps of:

performing a succession of ionizations of tissue, comprising a first ionization and at least one ionization subsequent to said first ionization, and selecting locations for ionizations subsequent to said first ionization, based on results of plasma analysis obtained following previous successive ionizations to identify extent and location of cancerous tissue.

3. The method of claim 2 further comprising the step of destroying said cancerous tissue using said laser.

* * * * *